United States Patent [19]

Loh

[11] Patent Number: 5,582,600
[45] Date of Patent: Dec. 10, 1996

[54] TRANSFER SET CONNECTOR WITH A LOCKING LID AND A METHOD OF USING THE SAME

[75] Inventor: Eric P. Loh, Park Ridge, Ill.

[73] Assignee: Baxter International Inc., Deerfield, Ill.

[21] Appl. No.: 510,890

[22] Filed: Aug. 3, 1995

[51] Int. Cl.[6] ................................. A61M 25/00
[52] U.S. Cl. ........................... 604/283; 604/905
[58] Field of Search ..................... 604/283, 280, 604/263, 192, 256, 905

[56] References Cited

U.S. PATENT DOCUMENTS

| | | |
|---|---|---|
| 4,645,494 | 2/1987 | Lee et al. . |
| 4,752,292 | 6/1988 | Lopez et al. . |
| 4,889,527 | 12/1989 | Herrli . |
| 4,895,570 | 1/1990 | Larkin . |
| 4,950,260 | 8/1990 | Bonaldo .......................... 604/283 |
| 5,137,524 | 8/1992 | Lynn et al. . |
| 5,195,957 | 3/1993 | Tollini . |
| 5,281,206 | 1/1994 | Lopez . |
| 5,330,450 | 7/1994 | Lopez . |
| 5,344,414 | 9/1994 | Lopez et al. . |
| 5,356,396 | 10/1994 | Wyatt et al. . |

*Primary Examiner*—John D. Yasko
*Attorney, Agent, or Firm*—Thomas S. Borecki; Charles R. Mattenson; Robert M. Barrett

[57] ABSTRACT

A connector assembly, preferably for medical use, is provided having a key component and a lid lock component to provide fluid communication between a fluid source and a destination such as a patient. The lid lock component includes a removably lockable lid. The lid is held closed in a locked position by stops located on at least one flexible arm integrally formed and selectively displaceable in the lid lock component. The lid is forced open by a longitudinal key within the key component. The key spreads the flexible arms so that the formerly locked lid is capable of passing through an opening created between the flexible arms to clear the stops. The lid is converted into a position parallel to the length of the lid lock component to provide fluid communication between tubing connected to the lid lock component. The connector assembly can be used for dialysis and the like.

19 Claims, 3 Drawing Sheets

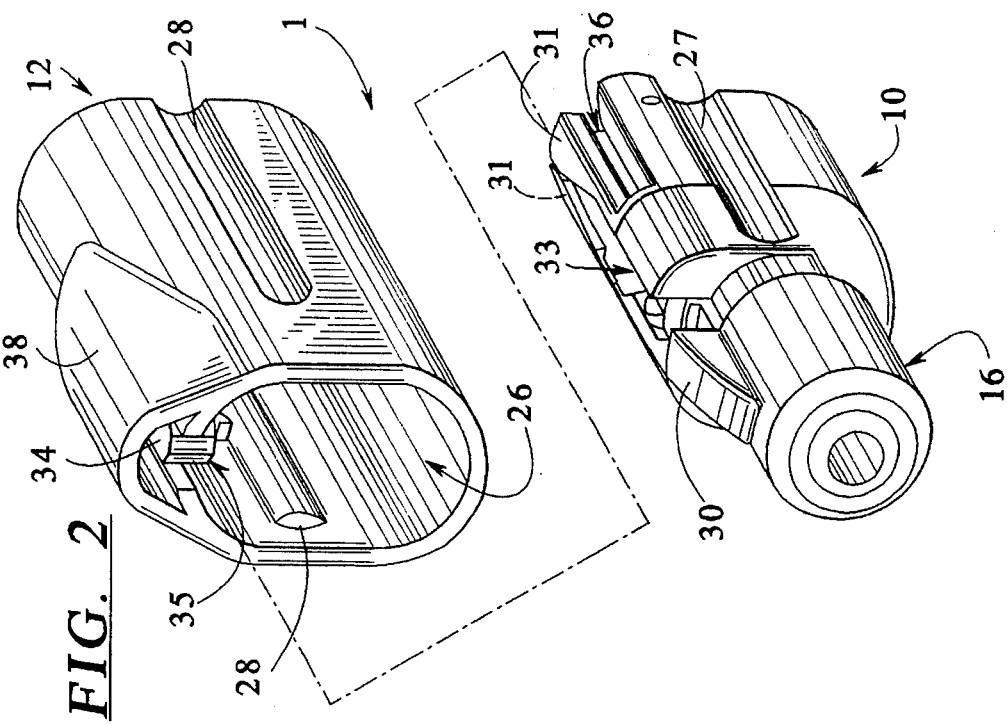
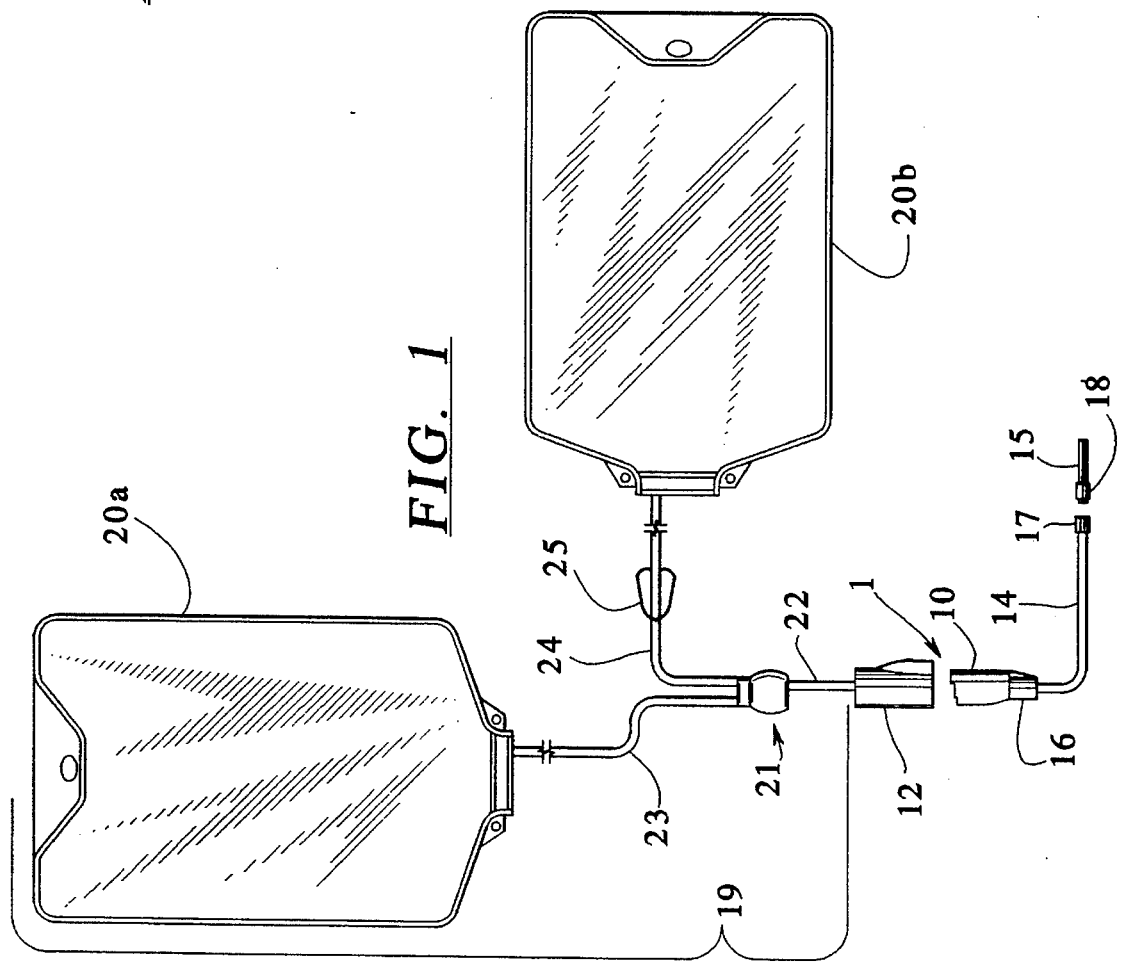

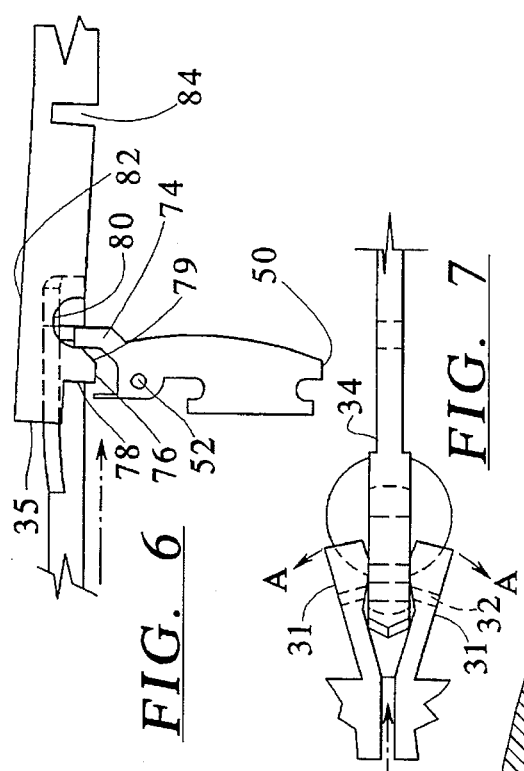
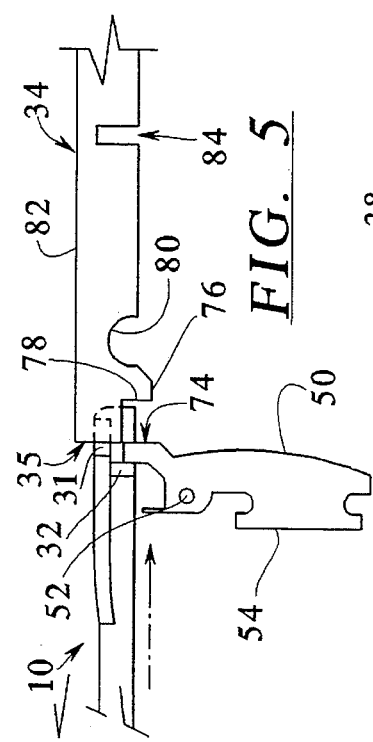
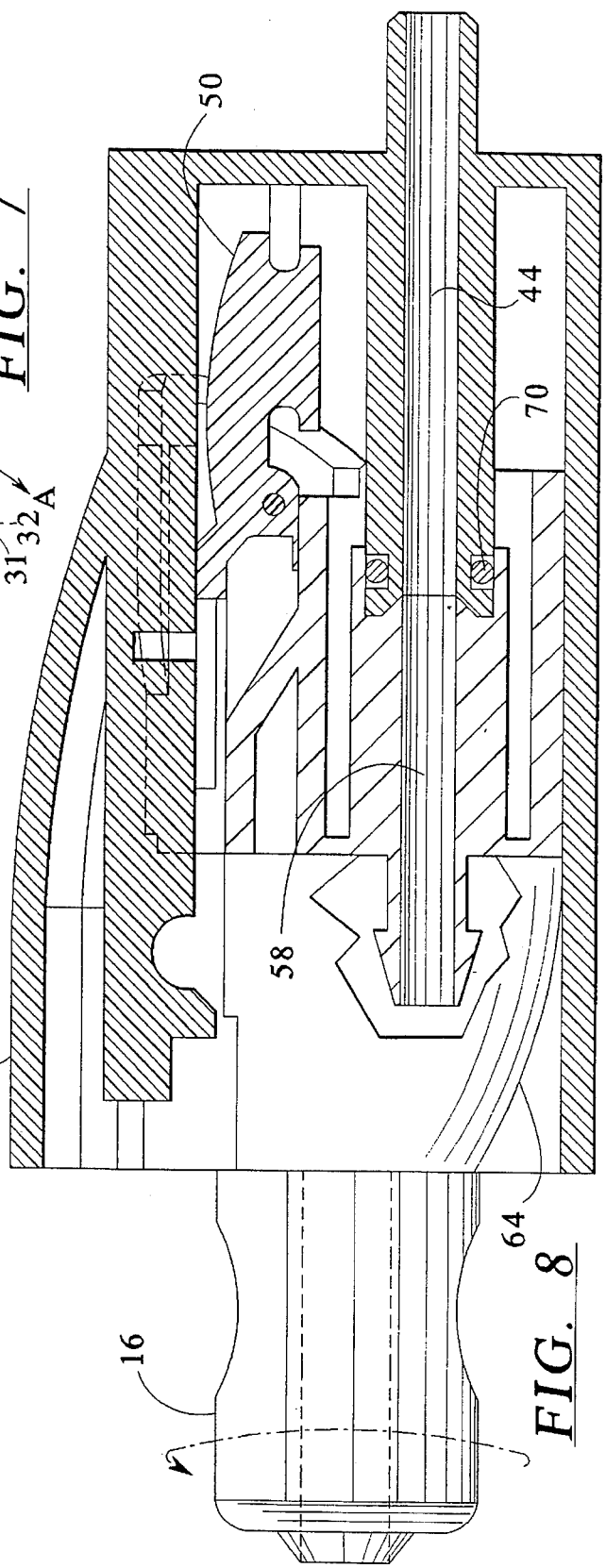

TRANSFER SET CONNECTOR WITH A LOCKING LID AND A METHOD OF USING THE SAME

BACKGROUND OF THE INVENTION

The present invention generally relates to a connector assembly for connecting a first length of tubing to a second length of tubing. More specifically, the present invention relates to a connector assembly having a locking hinged closure integrally formed with one component of the connector assembly and a cooperating component for opening the locking hinged closure when the two components are connected.

In a variety of industries, and for a variety of applications, it is necessary to create and provide a flow path. In many situations, most specifically in the medical industry, it is necessary to create sterile fluid flow paths.

It is, of course, generally known to provide fluid delivery to a patient for a variety of purposes, such as delivery of a medicament, provide nutrition, and peritoneal dialysis and the like. Such fluid delivery necessitates in many instances the creation of sterile flow paths. Such procedures often require the sterile flow paths to be disconnected and reconnected.

For example, it is known to use a cannula or a needle to inject into a patient a solution through the use of a length of tubing which is further connected to a container housing the solution. Often, an adaptor or other connector is provided for enabling fluid communication between the container and the patient through the tubing. For example, a connector may be provided at a port on the container to connect an end of the length of tubing to the container.

It is also well known to provide solutions to a patient, such as for peritoneal dialysis. In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. The proper acid-base electrolyte and fluid balance to be returned to the blood is achieved, and the dialysis solution is simply drained from the body cavity through the catheter.

This procedure is generally repeated three or four times daily for such a patient. Therefore, repeated connections and disconnections are required to be made from the system. Further, such a patient is often interrupted during administration of solution into the body requiring disconnection from the system.

At least three issues arise with respect to the disconnection and reconnection of a sterile flow path, such as that used for peritoneal dialysis. One requirement is that the system must provide a quick and a simple disconnection from the system. It is also required that a sterile, contaminant-free environment be maintained after disconnection. Further, the system must provide means for a simple reconnection to the system.

If dismantling of the entire set-up is required, a patient generally will not permit the interruption and will continue receiving the solution ignoring the interruption. On the other hand, if the disconnection and/or reconnection cannot be performed without contaminating the system, the contaminated system components or the entire system must be replaced. In the alternative, the contaminated components of the system must be sterilized before reuse of the system. Again, therefore, the patient will ignore the interruption and continue with the administration of solution from the system. At times, however, interruptions, such as emergencies, will require disconnection from the system.

A need, therefore, exists for an improved connector system for simplifying disconnection and reconnection of the components of the connector without contamination of the components of the system.

SUMMARY OF THE INVENTION

The present invention provides a connector assembly and a method of connecting a pair of connectors to provide fluid communication between a first length of tubing and a second length of tubing. The connector assembly incorporates a locking hinged lid providing sealed disconnection of the assembly. A sealed connection is provided by a sealing ring upon connection of the connectors.

To this end, in an embodiment, the present invention provides a connector assembly comprising a first component having an opening in fluid communication with a first length of tubing, the first component including a lid covering the opening and integrally formed and selectively displaceable means for removably locking the lid; and a second component having an interior in fluid communication with a second length of tubing, the second component including means for unlocking the lid wherein the first component is insertable into the interior of the second component providing fluid communication between the first length of tubing and the second length of tubing.

In an embodiment, the means for locking the lid includes at least one resilient arm.

In an embodiment, the means for locking the lid includes at least one stop capable of locking the lid.

In an embodiment, the connector assembly includes an o-ring to maintain a seal of the lid.

In an embodiment, the means for unlocking the lid includes a resilient key.

In an embodiment, the connector assembly includes a beveled front face formed on the key.

In an embodiment, the connector assembly further comprises a dome portion formed in the second component to allow movement of the key during mating of the components.

In an embodiment, the connector assembly further comprises a tubular member within the interior of the second component, the tubular member extending such that, when the second component mates with the first component, the opening of the first component is in fluid communication with the tubular member.

In an embodiment, the connector assembly includes an o-ring in the interior of the second component.

In another embodiment, the connector assembly further comprises a clamp constructed and arranged to selectively occlude flow through the tubing. The clamp may be rotatable about an axis defined along a length of the tubing.

In another embodiment of the present invention, a connector assembly for providing fluid communication between a first length of tubing and a second length of tubing is provided. The connector assembly comprises a first component connected to the first length of tubing, the first component having at least two flexible arms with stops formed thereon and further having a hinged lid maintained in a locked and closed position by the stops; and a second component having a means for opening the hinged lid and connected to the second length of tubing wherein connection of the first component to the second component opens the hinged lid and provides fluid communication between the first length of tubing and the second length of tubing.

In an embodiment, the connector assembly further comprises occluder means for selectively preventing and permitting flow through one of the lengths of tubing. The occluder means may be rotatable about an axis defined by the length of tubing.

In an embodiment, the connector assembly further comprises a beveled front end formed in the means for opening the lid; and an opening tab formed in the means for opening the lid.

In an embodiment, the connector assembly further comprises a beveled front end formed in the means for opening the lid, the beveled front end constructed and arranged to spread the flexible arms of the first component.

In an embodiment, the connector assembly further comprises a dome portion formed in the second component to provide clearance for the means for opening during connection of the first component and the second component, while enclosing the space and reducing chance for misuse.

In an embodiment, the first component and the second component are constructed and arranged to prevent misalignment.

In another embodiment of the present invention, a method for providing fluid communication between a first length of tubing connected to a patient and a second length of tubing connected to a fluid source is provided. The method comprises the steps of: providing a first component having an opening in fluid communication with the first length of tubing wherein the first component has a lid and integrally formed and selectively displaceable means for removably locking the lid; providing a second component in fluid communication with the second length of tubing wherein the second component includes means for locking the lid wherein; removably locking the lid over the opening in the first component; unlocking the opening by coupling the second component to the first component, thereby opening the lid to provide fluid communication between the first and second lengths of tubing.

In an embodiment, the fluid source is a source of dialysate.

In another embodiment, a connector assembly for creating fluid connections for use in medical procedures is provided. The connector assembly for creating fluid connections for use in medical procedures comprises: a first component having an opening in fluid communication with a first length of tubing, the first component including a lid covering the opening and integrally formed and selectively displaceable means for removably locking the lid; and a second component having an interior in fluid communication with a second length of tubing, the second component including means for unlocking the lid, wherein the first component is insertable into the interior of the second component providing fluid communication between the first length of tubing and the second length of tubing.

In an embodiment, the second length of tubing is connected to a source of medical fluid.

In an embodiment, the second length of tubing is connected to a source of dialysate.

In an embodiment, the connector assembly further comprises: a Y-set connector in fluid communication with the second length of tubing; a container of dialysate in fluid communication with the Y-set connector; a second container in fluid communication with the Y-set connector; and a catheter connected to the first length of tubing wherein the catheter is insertable into a patient to perform dialysis.

It is, therefore, an advantage of the present invention to provide a system and a method for connecting and disconnecting an assembly providing fluid communication between a source and a patient.

Another advantage of the present invention is to provide a system and a method for repeated connection and disconnection of a connector providing fluid communication between a source and a patient.

Yet another advantage of the present invention is to provide a simple connector that may readily connect and disconnect a first length of tubing from a second length of tubing in a sealed manner.

A still further advantage of the present invention is to provide a system and a method for connecting and disconnecting a connector between two lengths of tubing which may be easily performed by either a patient or other administrator.

Moreover, an advantage of the present invention is to provide a system and a method for connecting and disconnecting a connector between two lengths of tubing requiring few steps.

Another advantage of the present invention is to provide a compact, ergonomic system for connecting and disconnecting a connector between two lengths of tubing.

Additional features and advantages of the present invention are described in, and will be apparent from, the detailed description of the presently preferred embodiments and from the drawings.

BRIEF DESCRIPTION OF THE DRAWINGS

FIG. 1 illustrates an environmental view of an embodiment of a connector of the present invention in its disconnected state between a fluid source and a drain bag system at one end and a catheter to be inserted into a patient at another end.

FIG. 2 illustrates an exploded perspective view of an embodiment of the components of the connector of the present invention in a disconnected position.

FIGS. 5–7 illustrate detail views of embodiments of portions of the connector assembly showing successive connection steps and relationships of the key component and the lid lock component.

FIG. 8 illustrates a partially cut-away cross-sectional view of an embodiment of the connector assembly of the present invention in a connected position.

DETAILED DESCRIPTION OF THE PRESENTLY PREFERRED EMBODIMENTS

Figure 4:
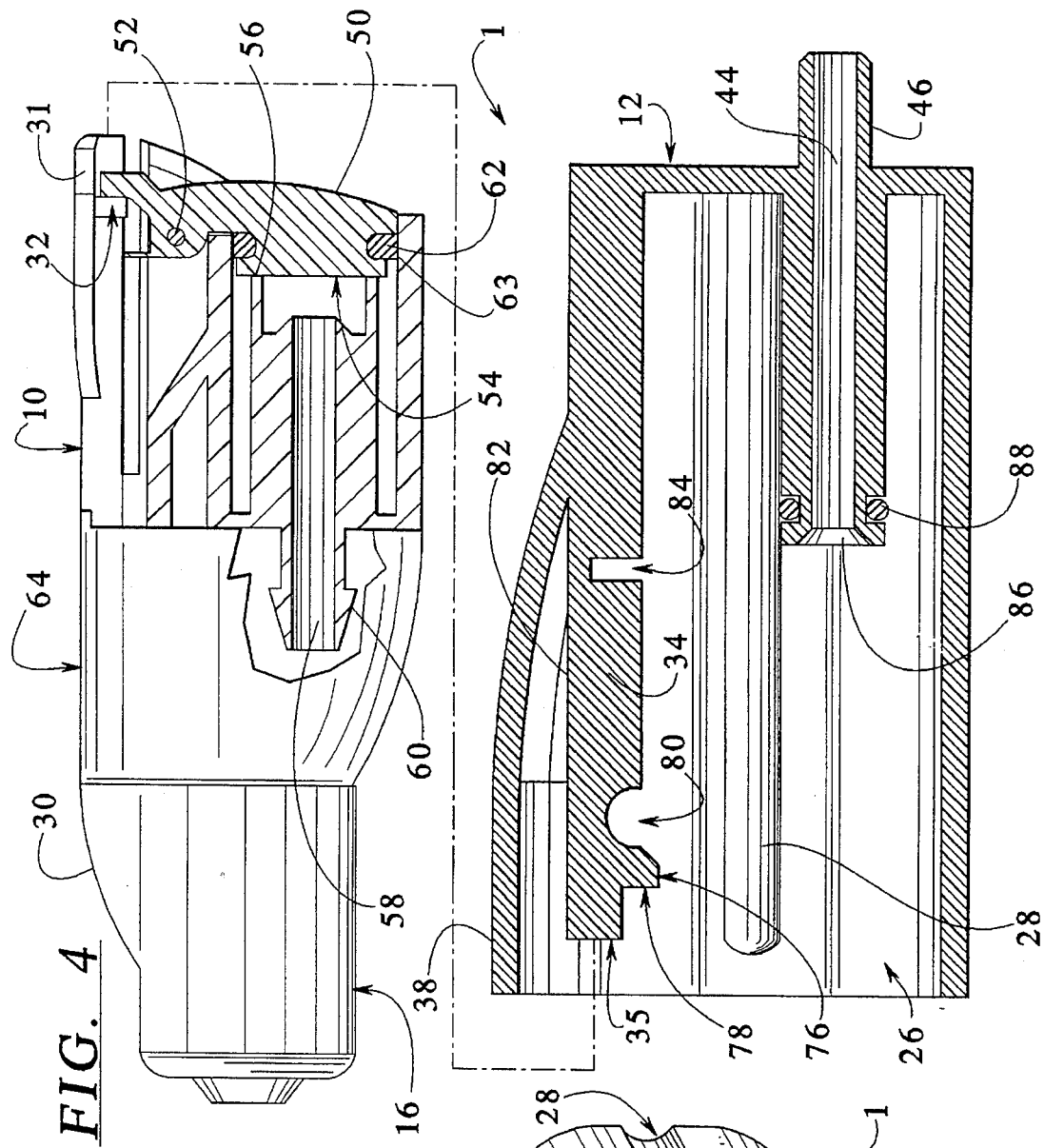
FIG. 4 illustrates a cross-sectional view of an embodiment of a key component and a partially cut-away cross-sectional view of an embodiment of a lid lock component of the connector of the present invention in a disconnected position.

The present invention provides a connector between two lengths of tubing or other conduit for selectively connecting and disconnecting the lengths of tubing. When connected, fluid communication is provided between a fluid source and a patient. Fluid, however, may be occluded from flowing when connected using an occluder connected with the connector.

Although the connector is designed specifically for use in procedures in the medical field, and more specifically for dialysis procedures, it should be noted that the connector can be used in other fields and for other applications.

Referring now to the drawings, FIG. 1 illustrates an environmental view of a system employing the connector of the present invention. The connector is generally illustrated at 1 and includes a lid lock component 10 and a key component 12. As illustrated in FIG. 1, in a preferred embodiment of the present invention, the lid lock component 10 is connected to a conduit 14. When in use, the conduit 14 may be attached via a catheter 15 to a patient. The conduit 14 has a twist clamp 16 at one end and a catheter connector 17 at another end. The catheter 15 may be connected to the catheter connector 17 via a titanium adapter 18 in a preferred embodiment.

The key component 12, on the other hand, in a preferred embodiment, may be connected to a Y-set generally illustrated at 19. The Y-set 19 includes two flexible containers 20a, 20b. Typically, for peritoneal dialysis, one of the flexible containers, for example, the flexible container 20a, is filled with a dialysate and the other flexible container 20b is empty and ready for use as a drain bag. The connector 1 of the present invention can readily be used in peritoneal dialysis and CAPD, for example. Other uses for the connector are, of course, possible.

In a preferred embodiment, a fill line 23 is connected to the flexible container 20a, and a drain line 24 is connected to the flexible container 20b. Opposite ends of both the fill line 23 and the drain line 24 are respectively connected to a Y-junction 21. Thus, the flexible containers 20a and 20b are attached to the key component 12 through the Y-junction 21 and a length of conduit 22 forming a portion of the Y-set 19.

A clamp 25 may be provided at any point along the length of the fill line 23 to control the flow of the dialysate as desired. The clamp 25 may also be connected to the drain line 24 during peritoneal dialysis, if desired. In another embodiment, the lid lock component 12 of the connector 1 may have the twist clamp 16 connected thereto for occluding fluid flow.

Figure 3:
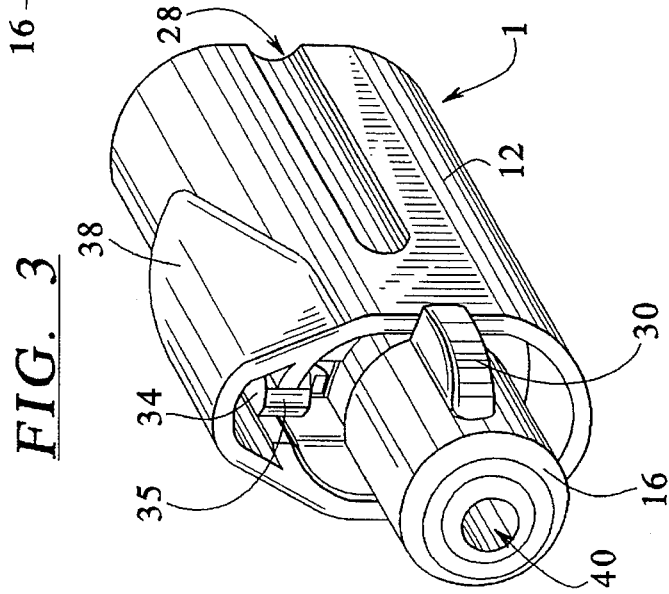
FIG. 3 illustrates a perspective view of an embodiment of the connector of the present invention in a connected position.

Referring now to FIGS. 2, 3 and 4, the connector 1 is illustrated. For example, FIG. 2 shows a perspective view of the lid lock component 10 and the key component 12 prior to connection. The lid lock component 10 has an exterior dimension designed to fit within an opening 26 of the key component 12 in sliding engagement. Further, the exterior of the lid lock component 10 is designed such that only one orientation of the lid lock component 10 may be received within the opening 26 of the key component 12.

To this end, a longitudinal guide groove 27 is formed in opposite sides of the lid lock component 10. The guide grooves 27 cooperatively mate with associated guide rails 28 formed in the key component 12 to strictly direct and align the lid lock component 10 within the opening 26 of the key component 12. Thus, the cooperating guide grooves 27 and guide rails 28 permit only one permissible operative orientation for the connector 1.

In an embodiment, the lid lock component 10 further includes the twist clamp 16 capable of axial rotation about the conduit 14. In the position illustrated in FIG. 2, the conduit 14 (see FIG. 1) is pinched closed by a pair of actuators (not shown) within the twist clamp 16. A tab 30 is provided on the twist clamp 16 to aid the user in turning the twist clamp 16, as well as to provide a visual indication of a locked or unlocked condition of the twist clamp 16.

FIG. 2 also shows the various features of the lid lock component 10. For example, a pair of flexible arms 31 having integrally formed stops 32 (see FIG. 4) and having a channel 33 therebetween are illustrated. A side channel 36 which allows for movement of the arms 31 during connection of the components 10,12 of the connector 1 is also provided.

Referring now to the key component 12 of the connector 1 as shown in FIG. 2, the key connector 12 includes a flexible longitudinal key 34 having a beveled front end face 35. The key component 12 also has a dome 38 to allow movement of the flexible longitudinal key 34 during connection and especially during disconnection (as illustrated in FIG. 6) of the connector 1 of the present invention.

FIG. 3 illustrates the connector 1 of the present invention in a connected position. Also, the tab 30 on the twist clamp 16 is shown rotated 90° from the position shown in FIG. 2. This indicates to the user that the connector 1 is in a state to allow fluid flow therethrough by means of a port 40 in the twist clamp 16.

Referring now to FIG. 4, the key component 12, shown in cross-section, is illustrated having the longitudinal key 34 extending within the opening 26 and a tubular member 44 extending substantially parallel to the longitudinal key 34 within the opening 26.

The lid lock component 10 illustrated in FIG. 4 also includes a locking hinged door 50 rotatable about an axle 52. The axle 52 allows the door 50, shown in FIG. 4 in a locked and closed position, to rotate approximately 90° to an open position shown in FIG. 8.

In addition, the tubular member 44 has a nipple 46 extending outwardly of the key component 12 to allow for the connection of the conduit 22, for example. The longitudinal key 34, during connection of the key component 12 to the lid lock component 10, forces rotation of the door 50 about the axle 52 as described below.

Referring still to FIG. 4, the door 50 has a sealing face 54 to provide for a seal against a surface 56 of a tubular channel 58 in an embodiment of the present invention. The tubular channel 58 preferably includes, at an opposite end, a barbed nipple 60 to securely connect the conduit 14 thereto, for example. The door 50 also seals the tubular channel 58 by providing an o-ring 62 to seal an interior wall 63. The lid lock component 10 also includes an adapter 64 intermediately connected to the twist clamp 16.

Referring now to FIGS. 4 and 8, the connector 1 is shown immediately prior to connection of the lid lock component 10 to the key component 12 (FIG. 4) and after connection therebetween (FIG. 8). The distinction between the connection and disconnection of the lid lock component 10 and the key component 12 is most clearly evident by the position of the door 50.

In the closed position shown in FIG. 4, the door 50 is substantially parallel to an end face of the lid lock component 10 and sealingly covers the tubular channel 58 to which the tubular member 44 subsequently connects in fluid communication as shown in FIG. 8 after the door 50 has rotated 90°. When connection of the key component 12 is desired with the lid lock component 10, the key component 12 is slidingly engaged around the lid lock component 10 allowing the longitudinal key 34 to unlock the door 50 locked by the stops 32 and to force the door 50 to rotate about the axle 52.

Referring now to FIGS. 5–7, an explanation of the steps involved in opening the door 50 of the lid lock connector 10 by using the longitudinal key 34 of the key component 12 follows. Referring specifically to FIG. 5, the locked closed door 50 is rotatable about the axle 52. The locked closed door 50 has a locking tab 74 which abuts against the stops 32 to hold the door 50 in a locked position until the longitudinal key 34 is used to open the door 50.

Also shown in FIG. 5, the longitudinal key 34 has an opening tab 76 which has a front face 78. The longitudinal key 34 also has an angled face 79 leading to an indented recess 80 to allow for clearance of the opening tab 76 during disconnection of the connector 1. The longitudinal key 34 also has a top surface 82 and a flex notch 84 to provide greater flexibility to the longitudinal key 34 when the longitudinal key 34 is retracted in a direction indicated by arrow x as illustrated in FIG. 6. FIG. 6 illustrates how the disconnection of the connector 1 is achieved. The longitudinal key 34 is retracted in the direction of arrow x until the locking tab 74 of the lid 50 is located within the indented recess 80. As the longitudinal key 34 is further retracted, the angled face 79 impinges on the locking tab 74. Continued retraction of the longitudinal key 34 will thus pull the angled face 79 over the top of the locking tab 74. However, in order for this action to occur, the longitudinal key 34 must be flexible; hence, the flex notch 84 is provided to allow the longitudinal key 34 to rise as the angled face 79 climbs over the locking tab 74. Also, the dome 38, as shown in FIG. 8, provides clearance for the longitudinal key 34 as it rises during retraction. In addition, a lesser amount of flex of the longitudinal key 34 is possible during connection.

As further illustrated with reference to FIG. 5, the beveled end face 35 of the longitudinal key 34 contacts and spreads the arms 31 of the lid lock component 10. Although the longitudinal key 34 is flexible, it has sufficient rigidity when in compression to spread the arms 31 to widen the channel 33. As shown from the top view of FIG. 7, the longitudinal key 34 proceeds through the channel 33 until it has sufficiently spread open the arms 31 in an outwardly direction as indicated by arrows A, thereby widening the channel 33. Then, the front face of the opening tab 76 of the longitudinal key 34 forces the locking tab 74 of the lid 50 through the widened channel 33. Thus, the longitudinal key 34 sufficiently opens the arms 31 so that the locking tab 74 is able to clear the stops 32 formed in the arms 31. The locking tab 74 of the now unlocked lid 50 can then pass through the spread arms 31.

When the key component 12 is connected to the lid lock component 10 as shown in FIG. 8, the door 50 is perpendicularly disposed with respect to an end face thereof. The opening 26 and the dome 38 are constructed and arranged to allow a clearance for the door 50 to swing therein as shown in FIG. 8. After connection of the key component 12 to the lid lock component 10, fluid communication between the Y-set 19 and the patient can be achieved.

As mentioned above, the lid lock component 10 further includes the twist clamp 16 partially rotatable about an axis parallel to a length of the conduit 14 between the lid lock component 10 and the patient. As mentioned above, within the twist clamp 16 are the pair of actuators (not shown). The twist clamp 16 rotates about the axis thereby deflecting the position of the actuators in a conduit compressed position and a flowing position.

Operation of the connector 1 includes insertion of the lid lock component 10 into the key component 12, wherein the longitudinal key 34 spreads the arms 31 to act against the stops 32 locking the door 50, thereby causing the door 50 to open.

Thus, the tubular member 44 cooperatively mates with the tubular channel 58 of the lid lock component 10. The tubular member 44 is guided adjacent to the opening (see FIG. 8) of the lid lock component 10 providing fluid communication through the key component 12 and the lid lock component 10.

As the lid lock component 10 and the key component 12 are further engaged following the unlocking and the opening of the door 50, the tubular member 44 of the key component 12 is sealingly engaged to the tubular channel 58 of the lid lock connector 10. To this end, the tubular member 44 may have a taper 86 for a lead-in to assist in the sealing engagement of the same. In another embodiment, the tubular member 44 may include an o-ring 88 to maintain the seal therebetween.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A connector assembly comprising:

a first component having an opening in fluid communication with a first length of tubing, the first component including a lid covering the opening and integrally formed and selectively displaceable means for removably locking the lid; and a second component having an interior in fluid communication with a second length of tubing, the second component including means for unlocking the lid wherein the first component is insertable into the interior of the second component providing fluid communication between the first length of tubing and the second length of tubing and further wherein the first component has an exterior dimension smaller than an exterior dimension of the second component at a point of connection between the first component and the second component.

2. The connector assembly of claim 1 wherein the means for locking the lid includes at least one resilient arm.

3. The connector assembly of claim 1 wherein the means for locking the lid includes at least one stop capable of locking the lid.

4. The connector assembly of claim 1 wherein the means for unlocking the lid includes a resilient key.

5. The connector assembly of claim 1 further comprising:

a ring to maintain a seal of the lid.

6. The connector assembly of claim 4 further comprising:

a dome portion formed in the second component to allow movement of the key during mating of the first component and the second component.

7. The connector assembly of claim 4 further comprising:

a beveled front face formed on the key.

8. The connector assembly of claim 1 further comprising:

a tubular member within the interior of the second component, the tubular member extending such that, when the second component mates with the first lock component to open the lid, the opening is in fluid communication with the tubular member.

9. The connector assembly of claim 1 further comprising:

a ring in the interior of the second component.

10. The connector assembly of claim 1 further comprising:

a taper in the interior of the second component.

11. The connector assembly of claim 1 further comprising:
   a clamp constructed and arranged to selectively occlude flow through one of the lengths of tubing.

12. The connector assembly of claim 11 wherein the clamp is rotatable about an axis defined along a length of the tubing.

13. A connector assembly for providing fluid communication between a first length of tubing and a second length of tubing, the assembly comprising:
   a first component connected to the first length of tubing, the first component having at least two flexible arms with stops formed thereon and further having a hinged lid maintained in a locked and closed position by the stops; and
   a second component having a means for opening the hinged lid and connected to the second length of tubing wherein coupling of the first component to the second component opens the hinged lid and provides fluid communication between the first length of tubing and the second length of tubing.

14. The connector assembly of claim 13 further comprising:
   occluder means for selectively preventing and permitting flow through one of the lengths of tubing.

15. The connector assembly of claim 13 further comprising:
   occluder means rotatable about an axis defined by the first length of tubing.

16. The connector assembly of claim 13 further comprising:
   a beveled front end formed in the means for opening the hinged lid; and
   an opening tab formed in the means for opening the hinged lid.

17. The connector assembly of claim 13 further comprising:
   a beveled front end formed in the means for opening the hinged lid, the beveled front end constructed and arranged to spread the at least two flexible arms of the first component.

18. The connector assembly of claim 13 further comprising:
   a dome portion formed in the second component to provide clearance for the means for opening during connection of the first component and the second component.

19. The connector assembly of claim 13 wherein the first component and the second component are constructed and arranged to prevent misalignment.

* * * * *